(12) United States Patent
Kalloo et al.

(10) Patent No.: US 6,572,629 B2
(45) Date of Patent: Jun. 3, 2003

(54) GASTRIC REDUCTION ENDOSCOPY

(75) Inventors: Anthony Nicolas Kalloo, Baltimore, MD (US); Sergey Veniaminovich Kantsevoy, Silver Spring, MD (US)

(73) Assignee: Johns Hopkins University, Baltimore, MD (US)

( * ) Notice: Subject to any disclaimer, the term of this patent is extended or adjusted under 35 U.S.C. 154(b) by 79 days.

(21) Appl. No.: 09/929,125

(22) Filed: Aug. 15, 2001

(65) Prior Publication Data

US 2002/0022851 A1 Feb. 21, 2002

Related U.S. Application Data

(60) Provisional application No. 60/225,784, filed on Aug. 17, 2000.

(51) Int. Cl.[7] .............................................. A61B 17/00
(52) U.S. Cl. ......................... 606/151; 606/139; 606/142
(58) Field of Search ................................. 606/153, 157, 606/148, 139, 113, 103; 128/898

(56) References Cited

U.S. PATENT DOCUMENTS

| | | | |
|---|---|---|---|
| 5,281,236 A | | 1/1994 | Bagnato et al. |
| 5,282,809 A | | 2/1994 | Kammerer |
| 5,324,298 A | | 6/1994 | Phillips |
| 5,345,949 A | * | 9/1994 | Shlain ........................ 128/898 |
| 5,391,176 A | | 2/1995 | De La Torre |
| 5,403,331 A | | 4/1995 | Chesterfield et al. |
| 5,405,352 A | | 4/1995 | Weston |
| 5,454,820 A | | 10/1995 | Kammerer |
| 5,466,241 A | | 11/1995 | Leroy |
| 5,472,446 A | | 12/1995 | De La Torre |
| 5,507,797 A | * | 4/1996 | Suzuki et al. ............... 606/140 |
| 5,549,633 A | | 8/1996 | Evans |
| 5,562,684 A | | 10/1996 | Kammerer |
| 5,571,120 A | | 11/1996 | Yoon |
| 5,599,300 A | | 2/1997 | Weaver |
| 5,681,331 A | | 10/1997 | De La Torre |
| 5,749,898 A | | 5/1998 | Schulze et al. |
| 5,769,862 A | | 6/1998 | Kammerer |
| 5,797,929 A | | 8/1998 | Andreas |
| 5,810,845 A | | 9/1998 | Yoon |
| 5,827,300 A | | 10/1998 | Fleega |
| 5,865,791 A | * | 2/1999 | Whayne et al. ............. 604/500 |
| 5,910,149 A | * | 6/1999 | Kuzmak ...................... 606/157 |
| 5,924,424 A | | 7/1999 | Stevens et al. |

OTHER PUBLICATIONS

Huibregtse ® Needle Knife Papillotomes Brochure; Wilson–Cook Medical GI Endoscopy; Jan. 1999; 5 pages.
Bard ® Eliminator ® Pet Biliary Balloon Dilators Brochure; Bard Interventional Products Division; Apr. 1997; 3 pages.
U.S. patent application Ser. No. 09/815,336 of Kalloo et al; filed Mar. 23, 2001.

* cited by examiner

Primary Examiner—David O. Reip
Assistant Examiner—Bradford C Pantuck
(74) Attorney, Agent, or Firm—Nixon & Vanderhye PC

(57) ABSTRACT

A technique is described for reducing the stomach cavity endoscopically, from within the stomach or, in the alternative, from within the peritoneal cavity via a wall of the digestive tract. This new approach for reducing gastric capacity uses a flexible endoscope and a specially adapted ligating loop that is secured at spaced locations about an inner periphery of the stomach. After attachment, the loop is constricted to draw together the associated gastric wall portions to reduce the food receiving cavity defined at the base of the esophagus. The ligating loop is preferably a slip knotted loop.

21 Claims, 7 Drawing Sheets

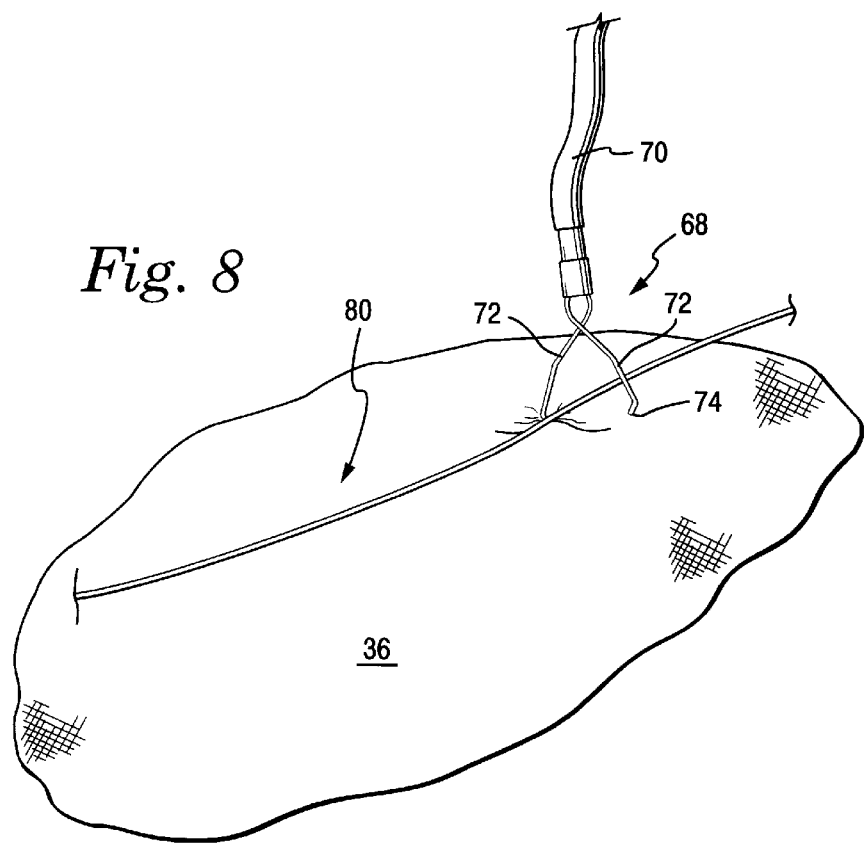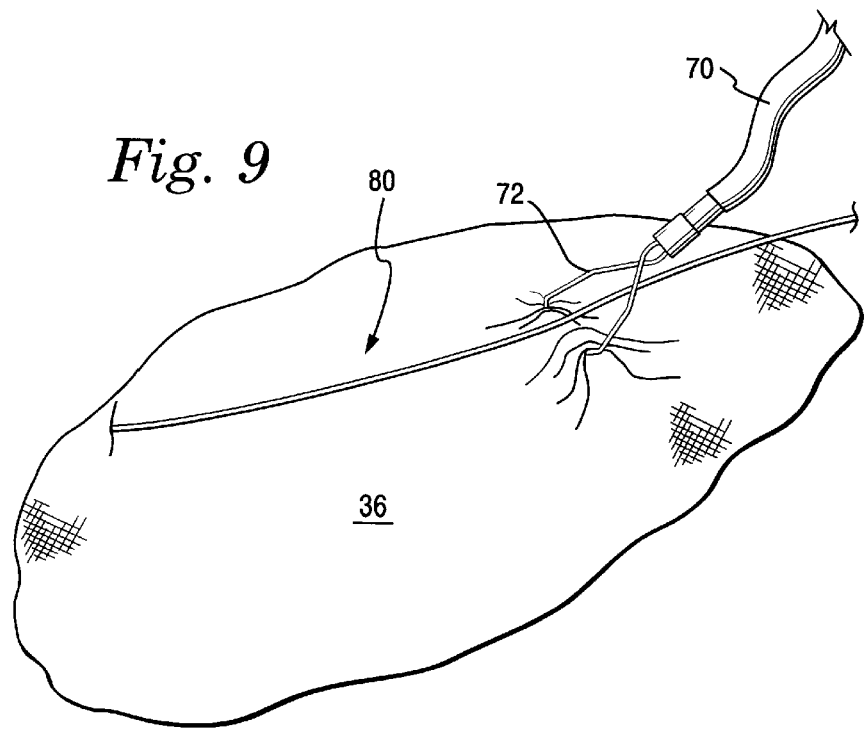

GASTRIC REDUCTION ENDOSCOPY

CROSS-REFERENCES TO RELATED APPLICATIONS

This application claims the benefit of U.S. Provisional Application Ser. No. 60/225,784, which was filed Aug. 17, 2000, the disclosure of which is incorporated herein by this reference.

BACKGROUND OF THE INVENTION

The present invention relates to gastric reduction and, more particularly, to a procedure and device for achieving a reduction in the size of the stomach, particularly in order to treat obesity in humans.

Gastric reduction surgery is conventionally performed to restrict food intake of a patient by decreasing the size of the stomach to a reservoir having a volume of on the order of about 15 mL. This operation thus limits the receptive capacity of the stomach and promotes weight loss in patients with severe obesity. The most commonly performed gastric reduction operation is vertical stapled gastroplasty. This procedure involves incision of the anterior abdominal wall and creation of a 10–15 ml pouch from the proximal stomach by use of 3–4 staples. This procedure may have numerous complications including rupture of the staple line, infection of the surgical incision, post operative hernias and the like. Moreover, due to the large amount of fat tissue in the anterior abdominal wall in the typical patient on whom this procedure is performed, poor healing of the operative wound may result. Furthermore prolonged post-operative bed rest after such extensive surgery predisposes obese patients to the development of deep vein thrombosis and possible pulmonary emboli, some with a potentially lethal outcome.

BRIEF SUMMARY OF THE INVENTION

We have developed a novel approach to achieving a reduction in the size of the stomach utilizing a flexible endoscope and, in a preferred embodiment, without any surgical incisions. More specifically, we have developed a technique for reducing the stomach cavity endoscopically, from within the stomach or, in the alternative, from within the peritoneal cavity via a wall of the digestive tract. Gastric reduction endoscopy utilizing either of these techniques will have an excellent cosmetic result as there are no incisions in the abdominal wall and thus no potential for post-surgical scars or hernias. Moreover, for the severely obese patient, the endoscopic approach eliminates the risks of an incision through the large amount of fat tissue in the anterior abdominal wall.

Our new approach for reducing gastric capacity uses a flexible endoscope and a specially adapted ligating loop. More specifically, the endoscopic procedure of the invention proposes to reduce the capacity of the stomach by securing a loop at spaced locations about the interior wall of the stomach and then constricting the loop to draw together the gastric wall, to thereby effectively reduce the food receiving cavity defined at the base of the esophagus. Accordingly to the presently preferred embodiment, the ligating loop is a slip knotted loop. As an alternative to an internal application of the loop, the loop can be applied to the exterior surface of the stomach. According to this alternative, we access the peritoneal cavity via an incision through the wall of the digestive tract, using the techniques described in our co-pending application No. 09/815,336, filed Mar. 23, 2001, the entire disclosure of which is incorporated herein by this reference, and then secure the loop to the exterior surface of the stomach. Constricting the thus applied loop will also achieve a reduction in the capacity of the stomach. Because the gastric reduction technique described hereinbelow proposes to collapse a portion of the stomach using a suitably disposed slip knotted loop, it will be appreciated that the gastric reduction technique may, in extraordinary circumstances, be reversed by severing the ligating or constricting loop, so that the stomach can return to its original capacity.

BRIEF DESCRIPTION OF THE DRAWINGS

These, as well as other objects and advantages of this invention, will be more completely understood and appreciated by careful study of the following more detailed description of the presently preferred exemplary embodiments of the invention taken in conjunction with the accompanying drawings, in which:

FIG. 8 is a schematic view showing a clip fixing device engaging the gastric wall as a step in the loop securing process;

FIG. 9 is a view similar to FIG. 8 showing the clip fixing device capturing the ligating loop, prior to closing the clip;

DETAILED DESCRIPTION OF THE INVENTION

Figure 1:
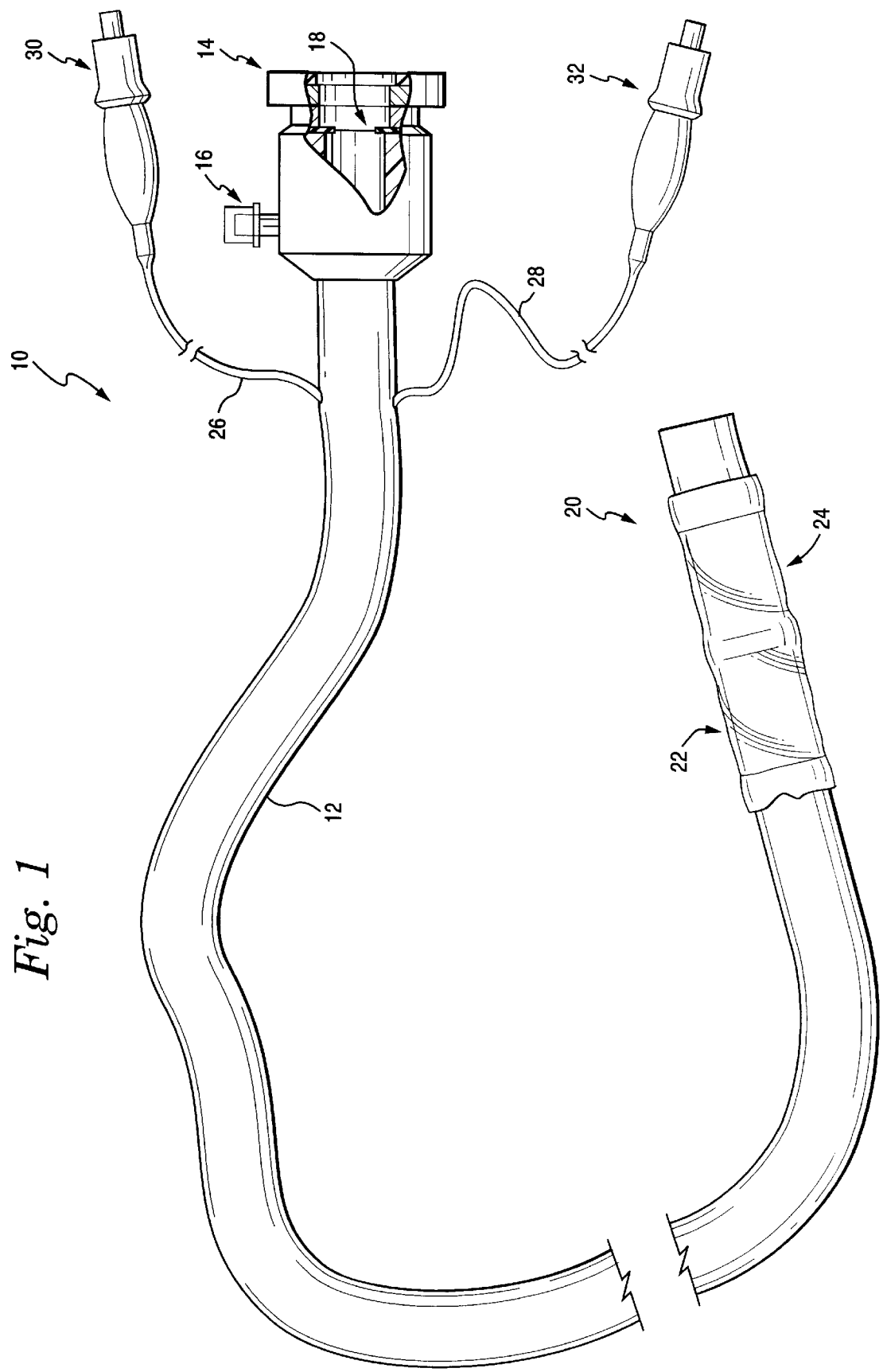
FIG. 1 is an illustration of an overtube according to an embodiment of the invention, with balloons deflated.

The invention is described detail below with reference to gastric reduction from within the stomach wall via the esophagus. The invention will also be described with reference to an alternative procedure in which peritoneal access is achieved via the stomach wall, or through the intestinal wall, and gastric reduction is achieved from within the peritoneal cavity.

Our novel endoscopic procedure will be described herein below with reference to various instruments and devices, some of which have been developed specifically for the implementation of this procedure. While some of the devices described herein are particularly adapted to this procedure, it is to be understood that commercially available devices may also be used to advantage to implement the process of the invention. Therefore, the endoscopic procedure of the invention is not to be limited to the use of the particular instruments described herein. The provision and use of devices specially adapted to this procedure may, however, facilitate its successful implementation. As will also be appreciated and understood from the disclosure to follow, the instruments and devices developed for the implementation of this procedure may also be used to advantage for the conduct of other medical procedures. Thus, those novel instruments and devices are not to be construed as limited to the uses therefor described herein with reference to gastric reduction.

To access and visualize the gastric cavity and/or the peritoneal cavity in accordance with the present invention, a passage for the sterile insertion of an endoscope and/or various surgical instruments is desirably provided. Such a sterile pathway is provided in the presently preferred embodiment of the invention by providing a special, sterile overtube 10 having a conduit 12 that is sized to receive an endoscope therethrough and is flexible so as to capable of flexing with the endoscope to navigate the digestive tract and be conducted and directed to a point adjacent to a target portion of the stomach wall. Typical endoscopes have an outer diameter on the order of about 10–15 mm. Accordingly, the overtube preferably has in interior passage for the endoscope having a diameter of at least about 10 mm and preferably in the range of about 10–20 mm.

To allow visualization of the vicinity of the distal end of the overtube from within the overtube, via the endoscope, during the insertion of the overtube, attachment of the constricting loop, and constriction thereof, described in greater detail below, in the presently preferred embodiment of the invention, at least a distal portion 20 of the overtube 10 is formed from a transparent material. For ease of manufacture, the entire overtube conduit 12 may be advantageously formed from a transparent material.

The proximal end of the overtube 10 is provided with a valve housing 14 that includes a chamber through which the endoscope passes into the lumen of the overtube conduit. The housing is configured to provide structural support for a valve/seal mechanism shown generally at 18. It is the function of the seal to prevent the escape of pressurized fluid through the overtube conduit 12 following insulation through port 16 to expand the gastric and/or peritoneal cavity for adequate examination. Any valve structure or mechanism now known or later developed to effect a seal about an endoscope or other instrument inserted through an access port to minimize escape of pressurized fluid can be provided to advantage at the proximal end of the overtube 10. In an exemplary embodiment, a suitable valve includes an aperture or septum seal having an aperture that allows it to receive and closely engage the outer surface of an endoscope inserted therethrough to form an airtight seal around the endoscope in operative use. This valve is formed from elastomeric material so that the aperture is biased to seal against the outer surface of the endoscope. In order to avoid significant friction forces, the aperture is preferably sized to a diameter slightly less then the outer diameter of the endoscope to be inserted therethrough. To accommodate a variety of instruments, however, the size of the aperture is preferably expandable without inducing substantial frictional forces to accommodate the various instrument sizes.

Although a valve having an expandable aperture has been mentioned in particular above, it is to be understood that a zero closure valve may be provided instead of or in addition to such an apertured sealing member.

Thus, the overtube prevents escape of air from the stomach and helps to deliver the endoscope and ligating device, described in greater detail herein below, in a sterile manner to and into the area of intervention. It is to be understood, however, that in the case of internal application of the ligating loop, in particular, the overtube is optional and may be omitted.

As mentioned above and described in greater detail herein below, as an alternative to securing the stomach constricting loop to the inner lining of the stomach, access to the peritoneal cavity is obtained through the wall of the digestive tract according to the technique described in our Application No. 09/815,336 and the loop is applied to the exterior of the stomach. Thus, the overtube illustrated in FIG. 1 generally corresponds to the overtube described in our co-pending Application No. 09/815,336, with the distal end 20 of the overtube adapted to be anchored to the wall of, e.g., the stomach, to provide a continuous path to and into the peritoneal cavity and to isolate the peritoneum from the gastric cavity. Such an anchoring and sealing function is provided by providing a pair of anchoring cuffs or balloons 22, 24 adjacent the distal end of the overtube. To selectively inflate and deflate the balloons, an inflation passage (not shown) for each balloon is defined longitudinally of the overtube, terminating proximally in respective inflation lines 26, 28 and inflation ports 30, 32. In the event loop application is limited to the inner lining of the stomach, the balloons and their associated inflation lines and ports can be omitted.

We have created a special endoscopic loop 80 for our gastric reduction procedure, which is delivered preferably via a passage in the endoscope into the area of the proximal stomach. The endoscopic loop is preferably formed from a high tensile strength material such as fishing line. The loop is secured to the inner wall of the stomach at spaced locations about an inner periphery of the stomach cavity. Accordingly to a preferred embodiment, the loop 80 is secured relative to the stomach wall with endoscopic clips 68 delivered via the endoscope 80. Once the loop has been circumferentially secured, the loop is constricted so as to draw together the associated gastric wall portions, thereby to effectively collapse a portion of the stomach 36 and substantially reduce the gastric cavity defined at the base of the esophagus 34. For the gastric reduction to be effectively permanent, the loop must be maintained in its constricted configuration. This may be achieved by fusing, clamping or otherwise adhering or mechanically fastening the adjacent ends of the constricted loop 80. According to a preferred embodiment of the invention, the loop is formed as a slip knotted loop so as to allow the constricting movement of the loop material but to effectively prevent the expansion of the loop, e.g. in response to a radial expansion force as might occur when the reduced gastric cavity is being filled with food. As will be appreciated, the slip knot 82 is desirably formed so as to define a knot of a diameter greater than an internal diameter of the endoscopic delivery tube 84 for the loop. In this way, the knot cannot be retracted into the tube 84 during loop constriction.

Figure 2:
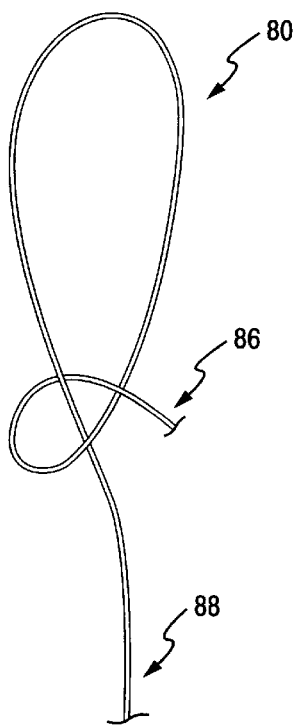
FIG. 2 is a view of a first step for forming a slip ligating knot according to a preferred embodiment of the invention.
Figure 3:
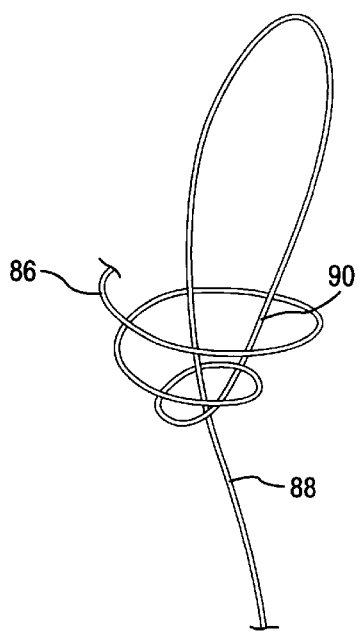
FIG. 3 is a view of a second step for forming a slip ligating knot according to a preferred embodiment of the invention.
Figure 4:
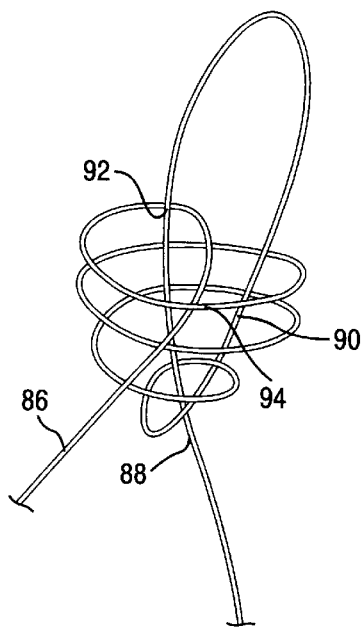
FIG. 4 is a view of a third step for forming a slip ligating knot according to a preferred embodiment of the invention.
Figure 5:
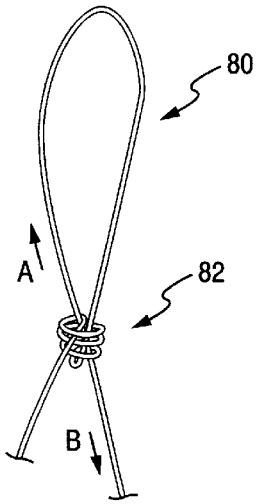
FIG. 5 is a view of a slip ligating knot formed according to the steps illustrated in FIGS. 2–4.

The slip knot 82 according to the presently preferred embodiment is illustrated in FIG. 5 and the formation thereof is illustrated in detail in the sequential views of FIGS. 2–4 As can be seen, to form the endoscopic loop 80 and slip knot 82, a length of material such as fishing line is looped to define a loop. For descriptive purposes, the loop 80 will be characterized as including a free end portion 86 and a feeder portion 88. The free end portion 86 of the line is looped as shown and fed behind the feeder portion 88 so as to define a single loop slip knot as shown in FIG. 2. Once this first loop has been formed, the free end of the line is twice looped around the feeder portion 88 and return portion 90 of the loop 80. The free end of the line may be looped more than twice about the feeder portion 88 and return portion 90 of the loop but two such further complete loops as illustrated in FIG. 4 is generally considered to be sufficient. Once the two further loops have been achieved, the free end 86 of the line is passed behind portion 92 of the loop and then threaded under loop 94 to complete the knot as shown in FIGS. 4 and 5. The illustrated knot is particularly adapted to the restricting process of the invention as the loop 80 defined distal to the slip knot 82 can be easily reduced in diameter by pulling feeder portion 88. However, the enlargement of the loop, particularly in a radial direction of the loop is substantially precluded by the slip knot 82. Rather an enlargement of the loop can effectively only be achieved by grasping the knot itself and pulling the feeder line 88 generally tangentially to the loop as shown by arrow A.

Figure 6:
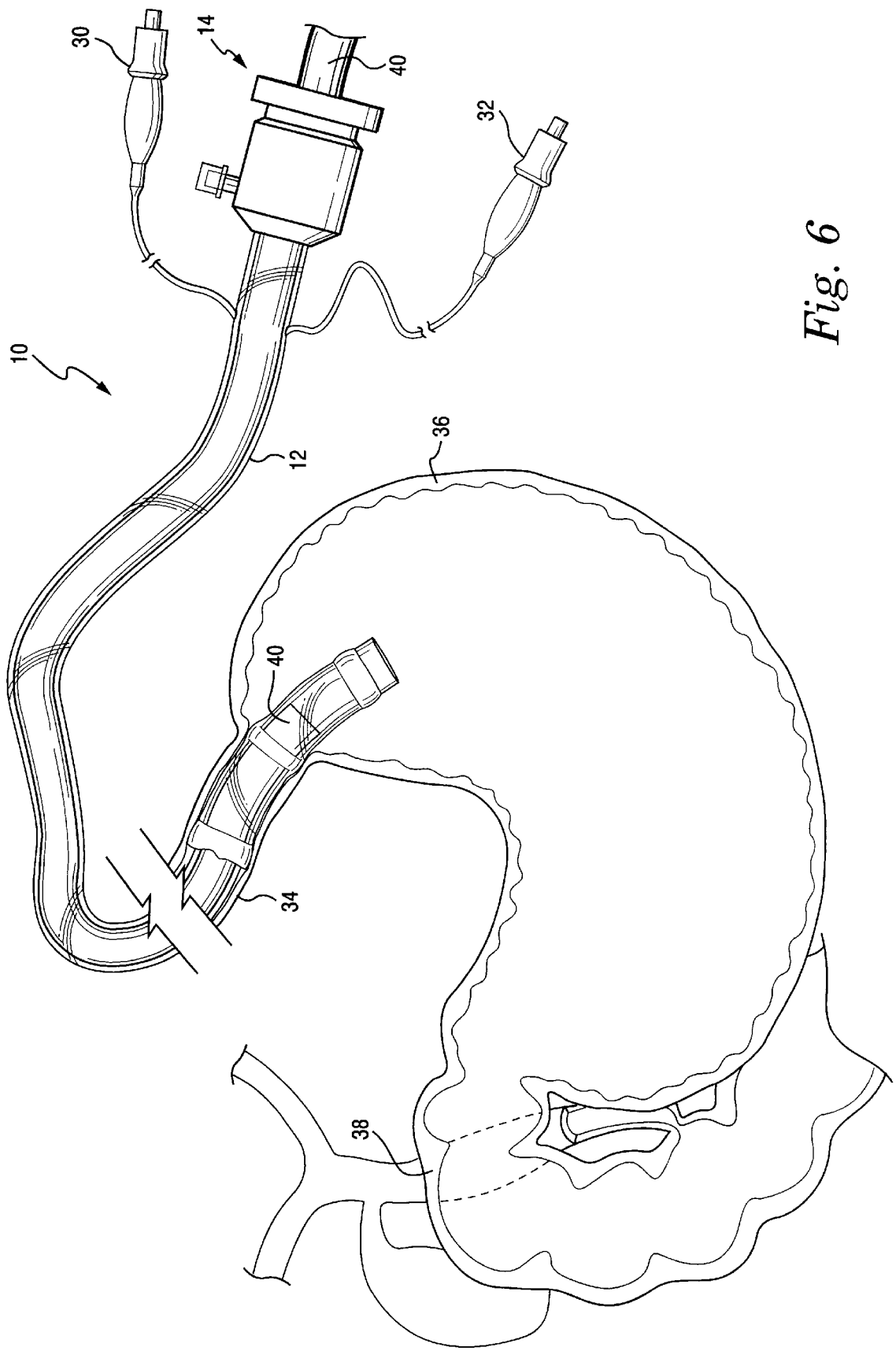
FIG. 6 is a schematic view showing the overtube with endoscope disposed therewithin located to a target portion of the stomach wall via the esophagus.

Referring to FIG. 6, a portion of the digestive tract including the distal end of the esophagus 34, the stomach 36, and the duodenum 38 are schematically shown as is an overtube 10 that has been fed through the esophagus 34 to terminate distally adjacent a target portion of the gastric wall. The overtube is desirably guided and directed into and within the stomach, in this example, or other segment of the digestive tract, with the aid of an endoscope 40 coaxially disposed therewithin.

Figure 7:
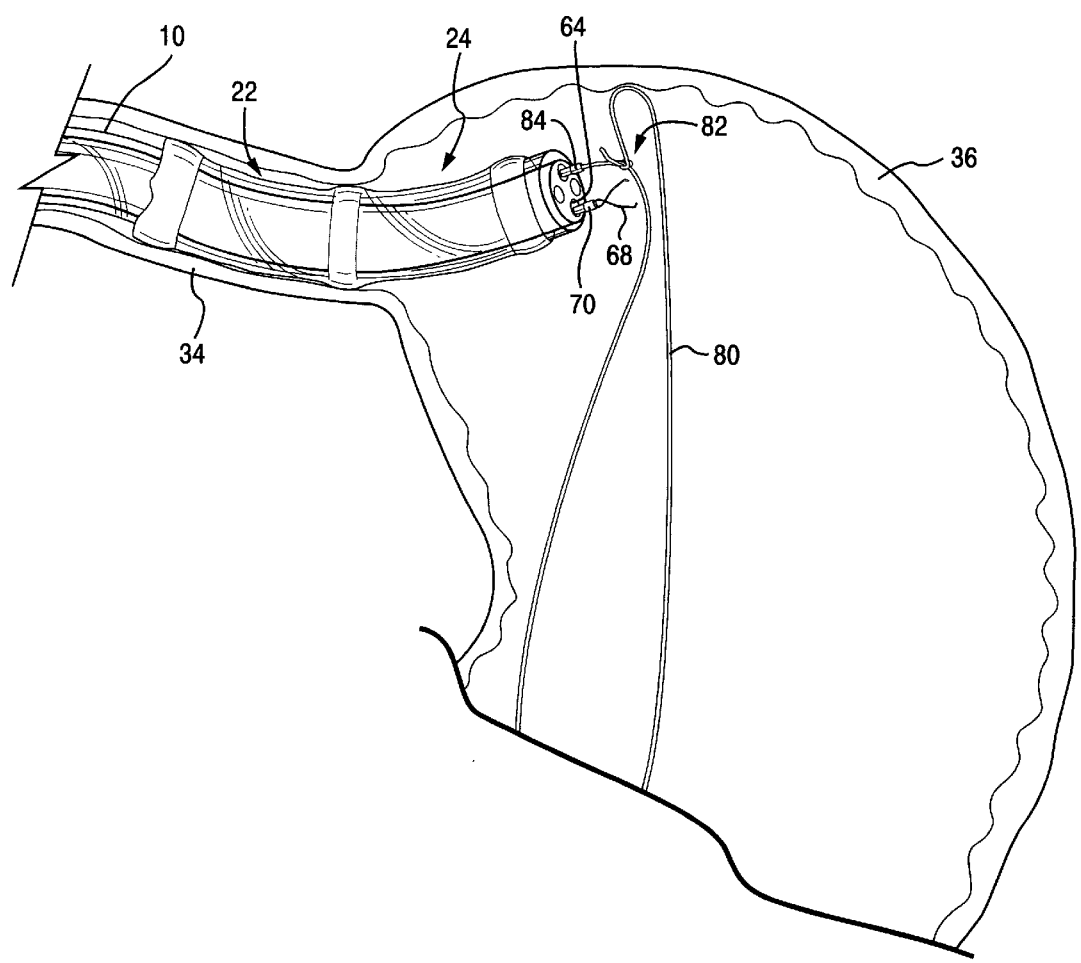
FIG. 7 is a schematic view showing the endoscope ready to apply clip fixing devices to secure the ligating loop to the gastric wall.

Once so located, with the distal end of the overtube and endoscope in opposed facing relation to the target site for loop application, a loop delivery device 84, having a preformed ligating loop 80, is advanced through an accessory channel of the endoscope 40 so as to protrude beyond the endoscope and dispose the loop 80 adjacent the wall surface of the stomach 86. As shown in FIG. 7, in this embodiment the loop is disposed in the stomach cavity but is as yet unattached to the stomach wall.

In accordance with a preferred embodiment of the invention, clip fixing devices 68 are used to secure the loop to the inner lining of the stomach. Clip fixing device applicators 70 for passage through an accessory channel of an endoscope and clip fixing devices 68 of various sizes are commercially available. Since clip fixing devices 68 are among the most easily manipulated and applied of the currently available endoscopically applied ligating devices, the use of clip fixing devices 68 is presently preferred, to secure the loop in place and hold the loop during constriction and thereafter. However, other mechanical fasteners such as sutures, staples and other commercially available ligating devices can be applied endoscopically as deemed necessary or desirable to secure the loop 80, provided that sliding movement of the loop therethrough is permitted so that loop constriction can be achieved.

Figure 10:
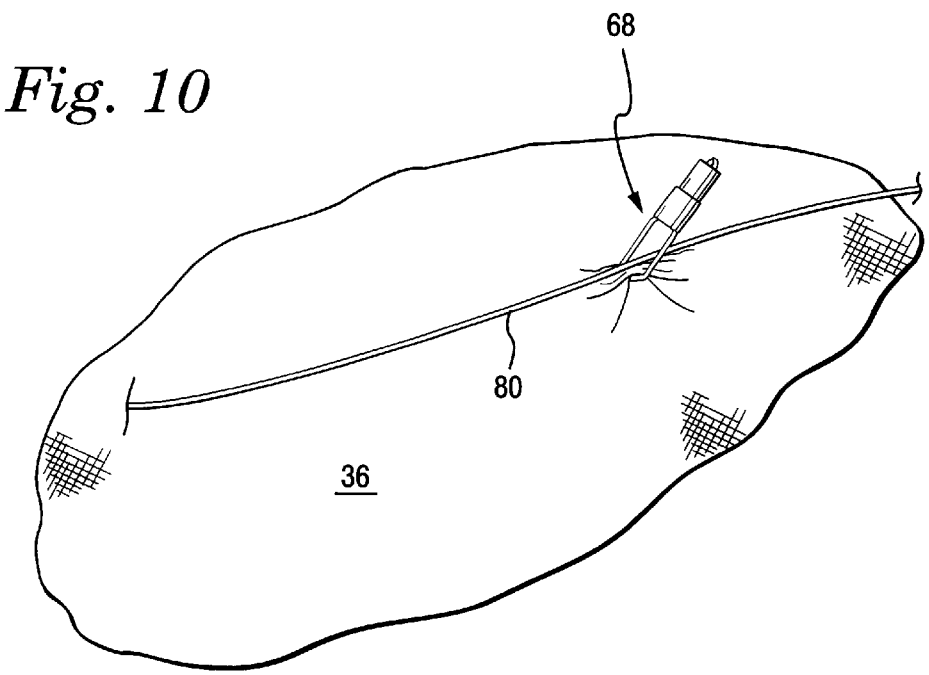
FIG. 10 is a schematic view showing the clip fixing device closed to secure the ligating loop to the gastric wall.
Figure 11:
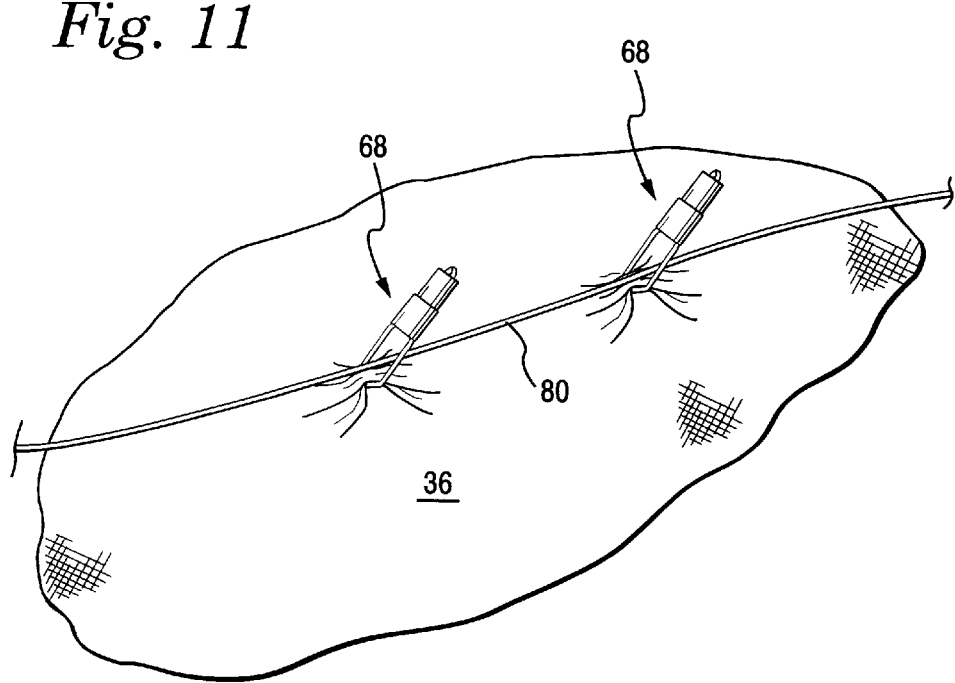
FIG. 11 is a schematic view showing clip fixing devices applied at adjacent but spaced locations to secure the ligating loop to the gastric wall in accordance with an exemplary embodiment.

FIG. 7 schematically illustrates the distal end of the endoscope 40 with a loaded clip fixing device applicator 70 projecting therebeyond, poised for application to secure the loop to the gastric lining. Referring to FIG. 8, the clip fixing device 68 includes first and second arms 72 terminating in a tissue gripping structure 74. To grasp the stomach lining, the distal end of one clip fixing device arm is contacted so as to engage the tissue on one side of the looped line 80, as shown in FIG. 8. Then, as shown in FIG. 9, the clip fixing device 68 is manipulated so that the distal end of the other clip arm engages the tissue on the opposite side of the looped line so that the clip 68 is engaged with tissue on both sides of the line. The clip fixing device actuator 70 is then actuated to close the clip fixing device 68 and clamp the tissue therebetween so as to secure the loop with respect to the stomach lining, while permitting sliding displacement of the line relative to the stomach wall during loop constriction, as shown in FIG. 10. Additional clip fixing devices 68 are sequentially applied, as illustrated in FIG. 11, at intervals of about 1–2 cm about the entire targeted interior periphery of the stomach lining so that the loop is secured thereabout.

The endoscopic clips are chosen to be of a suitable dimension to grasp a substantial segment of gastric tissue to ensure a firm and substantially permanent grasp of the stomach wall so as to preclude disengagement of the clip and/or tearing of the associated gastric tissue in the event the patient later consumes an excessive amount of food relative to the size of the gastric pouch.

As will be appreciated, by forming a special endoscopic loop as illustrated in FIGS. 2–5 and 7, to define a loop 80 of a size generally corresponding to the interior circumference of the target portion of the stomach and applying endoscopic clips 68 to secure the loop at spaced locations, about 1–2 cm apart, about the periphery of the stomach wall, the loop will be fully and securely engaged to the inner circumference of the stomach interior. Tightening the loop, by manually or mechanically pulling the feeder line 88 in direction B, the loop will be reduced in diameter and the associated portions of the wall of the stomach will be drawn together to close-off and generally collapse a portion of the stomach, leaving a pouch at the base of the esophagus of approximately 10–15 ml in volume. Once the endoscopic loop has been reduced to draw together the walls of the stomach, the endoscopic loop delivery tube 84 is retracted and/or fully removed. The feeder portion 88 of the endoscopic loop may then be severed with scissors, preferably through a another access port of the endoscope, to complete the procedure.

Figure 12:
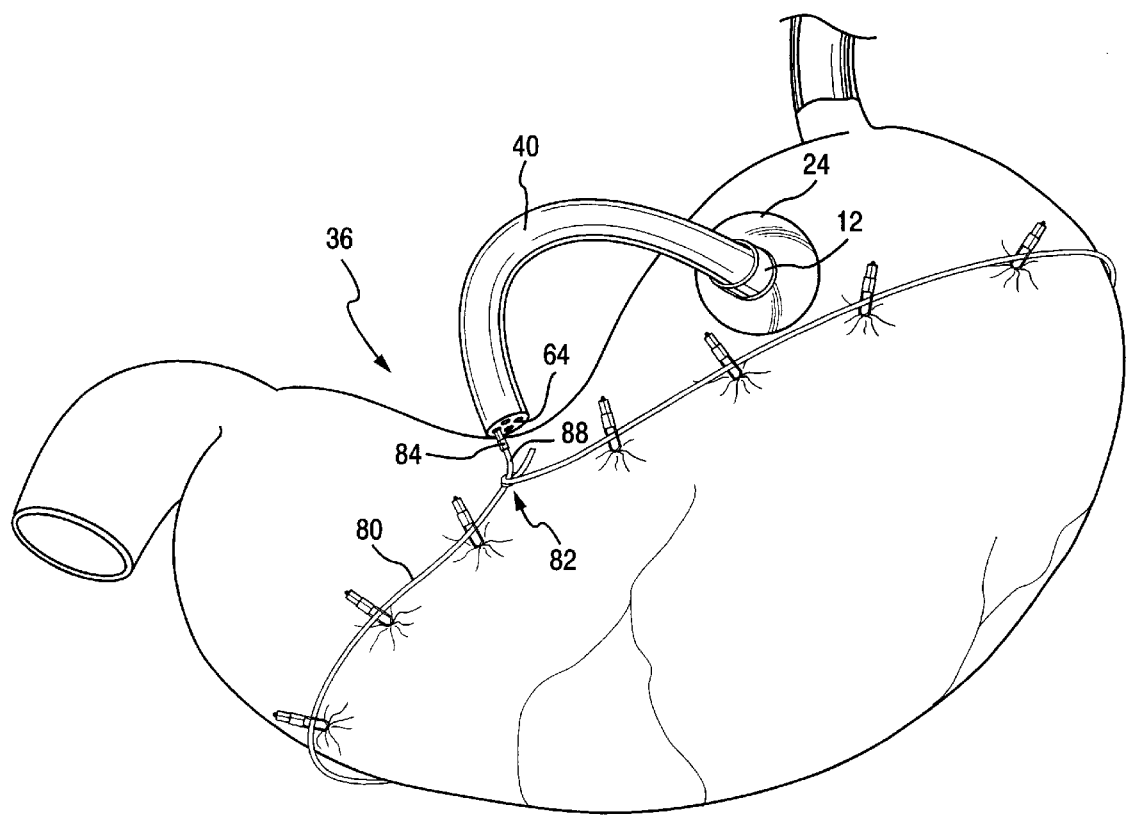
FIG. 12 is a perspective view illustrating an alternate embodiment of the invention and showing the surface of the stomach with the overtube anchored thereto and an endoscope projecting from the overtube, with a ligating loop disposed about the exterior of the stomach and secured thereto with clip fixing devices, before constriction.

In our copending Application No. 09/815,336 we describe a novel approach to diagnostic and therapeutic intervention in the peritoneal cavity. In that copending application, the entire disclosure of which is incorporated herein by this reference, we describe techniques for accessing the peritoneal cavity via a wall of the digestive tract, such as the stomach wall or the intestinal wall, so that examination of and/or a surgical procedure in the peritoneal cavity can be conducted via the wall of the digestive tract, using a flexible endoscope. Using the procedure described in that application, as an alternative to applying the endoscopic loop to the interior lining of the stomach, the endoscopic loop may be clipped to spaced locations about the exterior of the stomach wall to achieve a similar gastric reduction. More specifically, as illustrated in FIG. 12, using the technique described in copending application 09/815,336, an overtube 10 is anchored to the stomach wall, as shown, or to the wall of the intestine, to provide endoscopic access to the peritoneal cavity via the digestive tract. An endoscope 40 is fed into the peritoneal cavity and a loop delivery device 84 is fed therethrough, as described above with reference to FIG. 7. The suitably sized endoscopic loop 80 is then secured, e.g. clipped, at spaced locations about the exterior of the stomach wall to define a line of constriction for reducing the volume of the gastric cavity. Once the endoscopic loop has been clipped as desired to the target portion of the gastric wall, as shown in FIG. 12, the feeder line 88 is pulled to reduce the diameter of the endoscopic loop 80 and, thus, collapse the walls of the stomach to define a remaining pouch of about 10–15 ml for defining the functional gastric cavity thereafter. The feeder portion 88 of the loop is then severed as described above, and the overtube 10 is withdrawn. Finally, the incision is closed as described in application No. 09/815,336.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for reducing a volume of a gastric cavity of a mammal, said method comprising:
    positioning an endoscope to extend from an exterior of the mammal through a natural orifice into and along at least a portion of the digestive tract to a target wall portion in the digestive tract;
    disposing a loop of high tensile strength material adjacent one of an interior and an exterior wall surface of a stomach of the mammal;
    securing said loop of material to said wall surface at spaced locations about a periphery thereof;
    constricting said loop so as to reduce a diameter thereof, thereby to proximate said spaced locations of said wall surface and reduce a food receiving cavity of said stomach; and
    withdrawing said endoscope.

2. A method as in claim 1, wherein said step of positioning comprises positioning an elongated flexible conduit to extend from an exterior of the mammal through said natural orifice into and along at least said portion of the digestive tract to said target wall portion in the digestive tract and advancing said endoscope through said conduit.

3. A method as in claim 2, wherein an endoscope is disposed within said conduit during said positioning step and wherein said endoscope is manipulated to guide and direct said flexible conduit to said target wall segment.

4. A method as in claim 2, wherein said step of positioning said flexible conduit comprises positioning said flexible conduit through the patient's oral cavity and esophagus.

5. A method as in claim 2, further comprising advancing a distal end of said flexible conduit so that the distal end of said conduit extends through said target wall portion;
    anchoring said distal end with respect to said wall portion; and
    wherein said securing step comprises securing said loop of material to the exterior wall surface of the stomach of the mammal.

6. A method as in claim 5, wherein an endoscope is disposed within said conduit during said positioning step and wherein said endoscope is manipulated to guide and direct said flexible conduit to said target wall segment.

7. A method as in claim 5, wherein said securing step comprises applying a mechanical fastener to secure said loop to said exterior wall surface.

8. A method as in claim 7, wherein said step of applying a mechanical fastener comprises applying a ligating clip to capture said loop and engage said exterior wall surface.

9. A method as in claim 7, wherein said step of applying a mechanical fastener comprises disposing a clip applicator through an accessory channel of said endoscope, engaging a clip disposed at a distal end of said clip applicator with tissue on each lateral side of said material of said loop and actuating said clip so as to clamp said tissue and capture said material of said loop.

10. A method as in claim 5, wherein said target wall portion is a portion of the stomach wall.

11. A method as in claim 5, wherein said step of positioning said flexible conduit comprises positioning said flexible conduit through the patient's oral cavity and esophagus.

12. A method as in claim 5, further comprising, before said step of said disposing a loop of high tensile strength material, the step of forming a loop of high tensile strength material and forming a slip knot for controlling an expansion and contraction of said loop.

13. A method as in claim 5, further comprising providing a loop delivery device having a bore defined therethrough, threading said high tensile strength material through said bore of said loop delivery device; and
    forming a loop in said high tensile strength material adjacent a distal end of said loop delivery device.

14. A method as in claim 13, wherein said step of constricting said loop comprises pulling a proximal end of said high tensile strength material adjacent a proximal end of said loop delivery device.

15. A method as in claim 1, wherein said securing step comprises applying a mechanical fastener to secure said loop to said wall surface.

16. A method as in claim 15, wherein said step of applying a mechanical fastener comprises applying a ligating clip to capture said loop and engage said wall surface.

17. A method as in claim 15, wherein said step of applying a mechanical fastener comprises disposing a clip applicator through an accessory channel of said endoscope, engaging a clip disposed at a distal end of said clip applicator with tissue on each lateral side of said material of said loop and actuating said clip so as to clamp said tissue and capture said material of said loop.

18. A method as in claim 1, wherein said target wall portion is a portion of the stomach wall.

19. A method as in claim 1, further comprising, before said step of said disposing a loop of high tensile strength material, the step of forming a loop of high tensile strength material and forming a slip knot for controlling an expansion and contraction of said loop.

20. A method as in claim 1, further comprising providing a loop delivery device having a bore defined therethrough, threading said high tensile strength material through said bore of said loop delivery device; and
    forming a loop in said high tensile strength material adjacent a distal end of said loop delivery device.

21. A method as in claim 20, wherein said step of constricting said loop comprises pulling a proximal end of said high tensile strength material adjacent a proximal end of said loop delivery device.

* * * * *